US008876817B2

(12) United States Patent
Avitall et al.

(10) Patent No.: US 8,876,817 B2
(45) Date of Patent: Nov. 4, 2014

(54) ELECTROPHYSIOLOGY SYSTEM AND METHODS

(71) Applicant: Boston Scientific Scimed Inc., Maple Grove, MN (US)

(72) Inventors: Boaz Avitall, Whitefish Bay, WI (US); Josef V. Koblish, Sunnyvale, CA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 0 days.

(21) Appl. No.: 13/738,562

(22) Filed: Jan. 10, 2013

(65) Prior Publication Data

US 2013/0190747 A1  Jul. 25, 2013

Related U.S. Application Data

(60) Provisional application No. 61/585,083, filed on Jan. 10, 2012, provisional application No. 61/715,032, filed on Oct. 17, 2012.

(51) Int. Cl.
*A61B 18/14* (2006.01)

(52) U.S. Cl.
USPC .............................................. 606/34; 606/41

(58) Field of Classification Search
USPC ......................................... 606/27, 34, 35, 41
See application file for complete search history.

(56) References Cited

U.S. PATENT DOCUMENTS

| 5,398,683 | A | 3/1995 | Edwards et al. |
| 5,447,529 | A | 9/1995 | Marchlinski et al. |
| 5,718,701 | A | 2/1998 | Shai et al. |
| 6,064,905 | A | 5/2000 | Webster, Jr. et al. |
| 6,270,493 | B1 * | 8/2001 | Lalonde et al. ................. 606/23 |
| 2008/0161705 | A1 * | 7/2008 | Podmore et al. .............. 600/509 |
| 2008/0243214 | A1 | 10/2008 | Koblish |
| 2008/0312713 | A1 * | 12/2008 | Wilfley et al. .................. 607/41 |
| 2009/0163904 | A1 * | 6/2009 | Miller et al. .................... 606/33 |
| 2010/0168557 | A1 | 7/2010 | Deno et al. |
| 2010/0331658 | A1 | 12/2010 | Kim et al. |

OTHER PUBLICATIONS

International Search Report and Written Opinion issued in PCT/US2013/021013, mailed april 5, 2013, 14 pages.
Piorkowski, Christopher et al., "First in Human Validation of Impedance-Based Catheter Tip-to-Tissue Contact Assessment in the Left Atrium", Journal of Cardiovascular Electrophysiology, vol. 20, No. 12, Dec. 1, 2009, pp. 1366-1373.
Price, Adam et al., "Novel Ablation Catheter Technology that Improves Mapping Resolution and Monitoring of Lesion Maturation", The Journal of Innovations in Cardiac Rhythm Management, vol. 3, 2002, pp. 599-609.
Price, Adam et al., "PO3-39 Pin Electrodes Improve Resolution: Enhanced Monitoring of Radiofrequency Lesions in the Voltage and Frequency Domains", Heart Rhythm 2010, 31st Annual Scientific Sessions, May 12-15 in Denver Colorado.
Zachary, J.M. et al., "PO4-86 Pin Electrodes Provide Enhanced Resolution Enabling Titration of Radiofrequency Duration to Lesion Maturation", Heart Rhythm 2011, 32 Annual Scientific Sessions, May 4-7, San Francisco, CA.

* cited by examiner

*Primary Examiner* — Michael Peffley
*Assistant Examiner* — Daniel Fowler
(74) *Attorney, Agent, or Firm* — Faegre Baker Daniels LLP

(57) ABSTRACT

An electrophysiology system comprises an ablation catheter, a radiofrequency generator, and a mapping processor. The ablation catheter has a tissue ablation electrode and a plurality of microelectrodes distributed about the circumference of the tissue ablation electrode and electrically isolated therefrom. The plurality of microelectrodes define a plurality of bipolar microelectrode pairs. The mapping processor is configured to acquire output signals from the bipolar microelectrode pairs, compare the output signals, and generate an output to a display providing a visual indication of a characteristic of the microelectrodes and the tissue ablation electrode relative to myocardial tissue to be mapped and/or ablated.

7 Claims, 14 Drawing Sheets

US 8,876,817 B2

ELECTROPHYSIOLOGY SYSTEM AND METHODS

CROSS-REFERENCE TO RELATED APPLICATION

This application claims the benefit of Provisional Application No. 61/715,032, filed Oct. 17, 2012, and Provisional Application No. 61/585,083 filed Jan. 10, 2012, each of which is incorporated herein by reference in its entirety.

TECHNICAL FIELD

The present disclosure relates to therapies for cardiac conditions. More particularly, the present disclosure relates to methods and systems for ablation of cardiac tissue for treating cardiac arrythmias.

BACKGROUND

Aberrant conductive pathways disrupt the normal path of the heart's electrical impulses. For example, conduction blocks can cause the electrical impulse to degenerate into several circular wavelets that disrupt the normal activation of the atria or ventricles. The aberrant conductive pathways create abnormal, irregular, and sometimes life-threatening heart rhythms called arrhythmias. Ablation is one way of treating arrhythmias and restoring normal contraction. The sources of the aberrant pathways (called focal arrhythmia substrates) are located or mapped using mapping electrodes situated in a desired location. After mapping, the physician may ablate the aberrant tissue. In radio frequency (RF) ablation, RF energy is directed from the ablation electrode through tissue to an electrode to ablate the tissue and form a lesion.

SUMMARY

In Example 1, the present invention is an electrophysiology method comprising advancing a distal portion of an ablation catheter intravascularly to a location proximate myocardial tissue within a chamber of a heart. The distal portion of the ablation catheter includes a tissue ablation electrode and a plurality of microelectrodes circumferentially distributed about the tissue ablation electrode and electrically isolated therefrom. The tissue ablation electrode is configured to apply ablation energy to the myocardial tissue, and the plurality of microelectrodes define a plurality of bipolar microelectrode pairs, each bipolar microelectrode pair configured to generate an output signal. The method further comprises acquiring the output signals from each of the bipolar microelectrode pairs, and comparing an amplitude of the output signal from each of the bipolar microelectrode pairs to the amplitudes of the output signals from the other of the plurality of bipolar microelectrode pairs. The method further comprises displaying to a clinician a visual indication of a proximity of the tissue ablation electrode to the myocardial tissue. The visual indication includes an indication that the tissue ablation electrode is in contact with the myocardial tissue if a difference between the amplitude of any one of the output signals and the amplitude of any one or more of the other output signals exceeds a predetermined threshold, an indication that the tissue ablation electrode is not in contact with the myocardial tissue if the difference between the amplitude of any one of the output signals and the amplitude of any one or more of the other output signals does not exceed a predetermined threshold.

In Example 2, the method of Example 1, wherein the acquiring and comparing steps are performed by a mapping processor operatively coupled to the microelectrodes.

In Example 3, the method of either of Examples 1 or 2, wherein the plurality of microelectrodes include three microelectrodes defining first, second and third bipolar microelectrode pairs.

In Example 4, the method of Example 3, wherein the three microelectrodes are disposed at the same longitudinal position along the tissue ablation electrode.

In Example 5, the method of any of Examples 1-4, further comprising displaying to the clinician a visual indication of an orientation of the tissue ablation electrode relative to the myocardial tissue based on the amplitudes of the output signals from the first, second and third bipolar microelectrode pairs.

In Example 6, of any of Examples 1-5, further comprising acquiring output signals from one or more ring electrodes located on the ablation catheter proximal to the tissue ablation electrode, comparing the output signal from each bipolar microelectrode pair with the ring electrode output signals to identify intrinsic cardiac activation signals in the bipolar microelectrode pair signals, and generating an output to a display indicating a gap in an ablation lesion set at the location of any bipolar microelectrode pairs that sensed the intrinsic cardiac activation signals.

In Example 7, the method of any of Examples 1-6, wherein the ablation catheter further comprises a plurality of irrigation ports in the tissue ablation electrode fluidly and operatively coupled to an irrigation fluid reservoir and pump.

In Example 8, the method of any of Examples 1-7, wherein the ablation catheter further includes a proximal handle having a control element for manipulation by a user, and wherein advancing the distal portion of the ablation catheter includes manipulating the control element to deflect the distal portion for positioning the tissue ablation electrode adjacent to the myocardial tissue.

In Example 9, an electrophysiology system comprising an ablation catheter, a radiofrequency (RF) generator, and a mapping processor. The ablation catheter includes a flexible catheter body having a distal portion, a tissue ablation electrode, and a plurality of microelectrodes. The tissue ablation electrode is configured to apply ablation energy to the myocardial tissue. The plurality of microelectrodes are circumferentially distributed about the tissue ablation electrode and electrically isolated therefrom, and define a plurality of bipolar microelectrode pairs, each bipolar microelectrode pair configured to generate an output signal. The RF generator is operatively coupled to the tissue ablation electrode for generating the ablation energy to be conveyed to the tissue ablation electrode. The mapping processor is configured to acquire the output signals from each of the bipolar microelectrode pairs, compare an amplitude of the output signal from each of the bipolar microelectrode pairs to the amplitudes of the output signals from the other of the plurality of bipolar microelectrode pairs, and generate an output to a display to provide a clinician with a visual indication of a proximity of the tissue ablation electrode to the myocardial tissue. The visual indication includes an indication that the tissue ablation electrode is in contact with the myocardial tissue if a difference between the amplitude of any one of the output signals and the amplitude of any one or more of the other output signals exceeds a predetermined threshold, and an indication that the tissue ablation electrode is not in contact with the myocardial tissue if the difference between the amplitude of any one of the output signals and the amplitude of any one or more of the other output signals does not exceed a predetermined threshold.

In Example 10, the system of Example 9, wherein the plurality of microelectrodes include three microelectrodes defining first, second and third bipolar microelectrode pairs.

In Example 11, the system of claim either of Examples 9 or 10, wherein the three microelectrodes are disposed at the same longitudinal position along the tissue ablation electrode.

In Example 12, the system of any of Examples 9-11, wherein the mapping processor is further configured to generate an output to a display to provide the clinician with a visual indication of an orientation of the tissue ablation electrode relative to the myocardial tissue based on the amplitudes of the output signals from the first, second and third bipolar microelectrode pairs.

In Example 13, the system of any of Examples 9-12, wherein the mapping processor is further configured to acquire output signals from one or more ring electrodes located on the ablation catheter proximal to the tissue ablation electrode, compare the output signals from the bipolar microelectrode pairs with the ring electrode output signals to identify sensed intrinsic cardiac activation signals in the bipolar microelectrode pair output signals, and generate an output to the display indicating a gap in an ablation lesion pattern at the location of the bipolar microelectrode pairs that sensed the intrinsic cardiac activation signals.

In Example 14, the system of any of Examples 9-13, wherein the ablation catheter further comprises a plurality of irrigation ports in the tissue ablation electrode fluidly and operatively coupled to an irrigation fluid reservoir and pump.

In Example 15, the system of any of Examples 9-14, wherein the ablation catheter further includes a proximal handle having a control element for manipulation by a user, and wherein the distal portion of the ablation catheter is deflectable upon manipulation of the control element.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
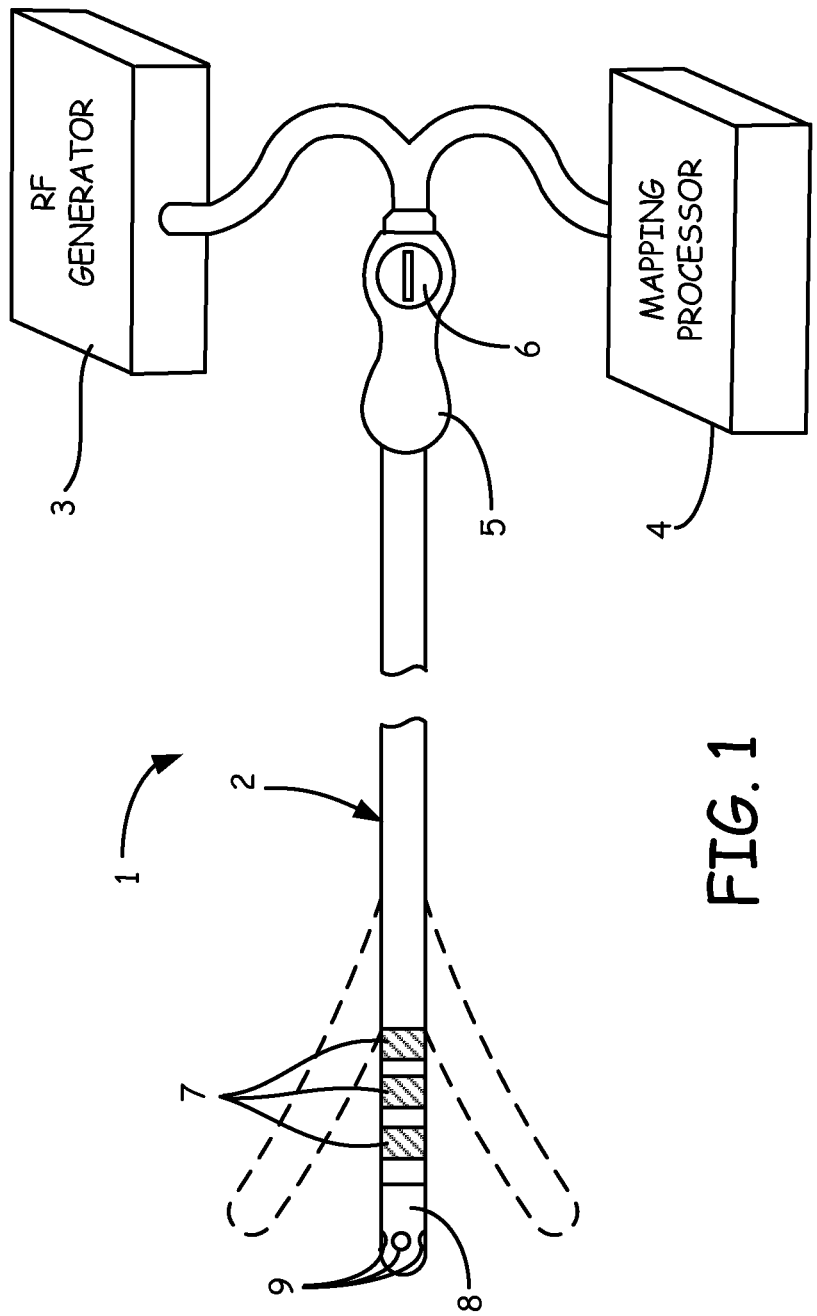
FIG. 1 is a schematic illustration of a radio frequency (RF) ablation system 1 according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic illustration of a radio frequency (RF) ablation system 1 according to one embodiment of the present invention. As shown in FIG. 1, the system 1 includes an ablation catheter 2, an RF generator 3, and a mapping processor 4. The ablation catheter 2 is operatively coupled to both the RF generator 2 and the mapping processor 4, as will be described in greater detail herein. As further shown, the ablation catheter 2 includes a proximal handle 5 having a control knob 6, a flexible body having a distal portion including a plurality of ring electrodes 7, a tissue ablation electrode 8, and a plurality of mapping microelectrodes 9 (also referred to herein as "pin" electrodes) disposed within and electrically isolated from the tissue ablation electrode 8.

In various embodiments, the ablation catheter 2 is configured to be introduced through the vasculature of the patient, and into one of the chambers of the heart, where it can be used to map and ablate myocardial tissue using the microelectrodes 9 and the tissue ablation 8. Thus, the tissue ablation electrode 8 is configured to apply ablation energy to the myocardial tissue. In the illustrated embodiment, the ablation catheter 2 is steerable, such that the distal portion can be deflected (as indicated by the dashed outlines in FIG. 1) by manipulation of the control knob 6. In other embodiments, the distal portion of the ablation catheter 2 has a pre-formed shape adapted to facilitate positioning the tissue ablation electrode 8 and the microelectrodes 9 adjacent to specific target tissue. In one such embodiment, the pre-formed shape is generally circular or semi-circular and is oriented in a plane transverse to the general direction of the catheter body.

In various embodiments, the microelectrodes 9 are circumferentially distributed about the tissue ablation electrode 8 and electrically isolated therefrom. The microelectrodes 9 can be configured to operate in unipolar or bipolar sensing modes. In various embodiments, the plurality of microelectrodes 9 define a plurality of bipolar microelectrode pairs, each bipolar microelectrode pair being configured to generate an output signal corresponding to a sensed electrical activity of the myocardial tissue proximate thereto. The generated output signals from the microelectrodes 9 can be sent to the mapping processor 4 for processing as described herein.

Figure 3:
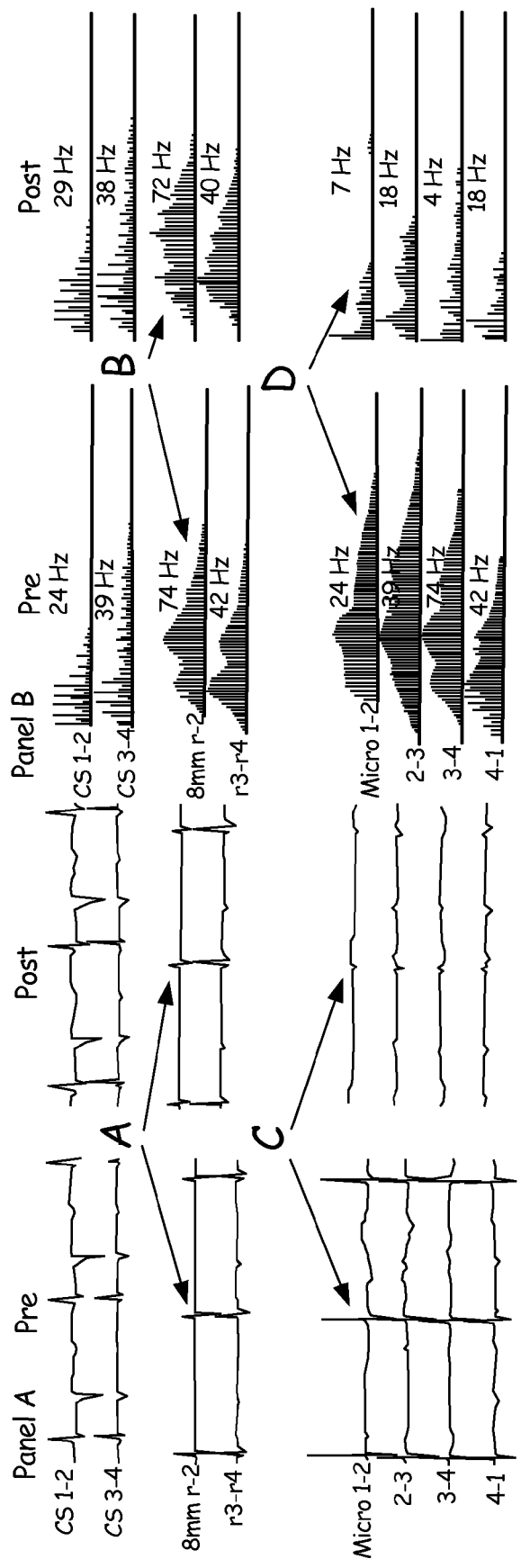
FIG. 3 illustrates a comparison between changes in voltage (panel A) and frequency spectra (panel B) pre- and post-ablation for each of the catheters illustrated in FIG. 2.
Figure 4:
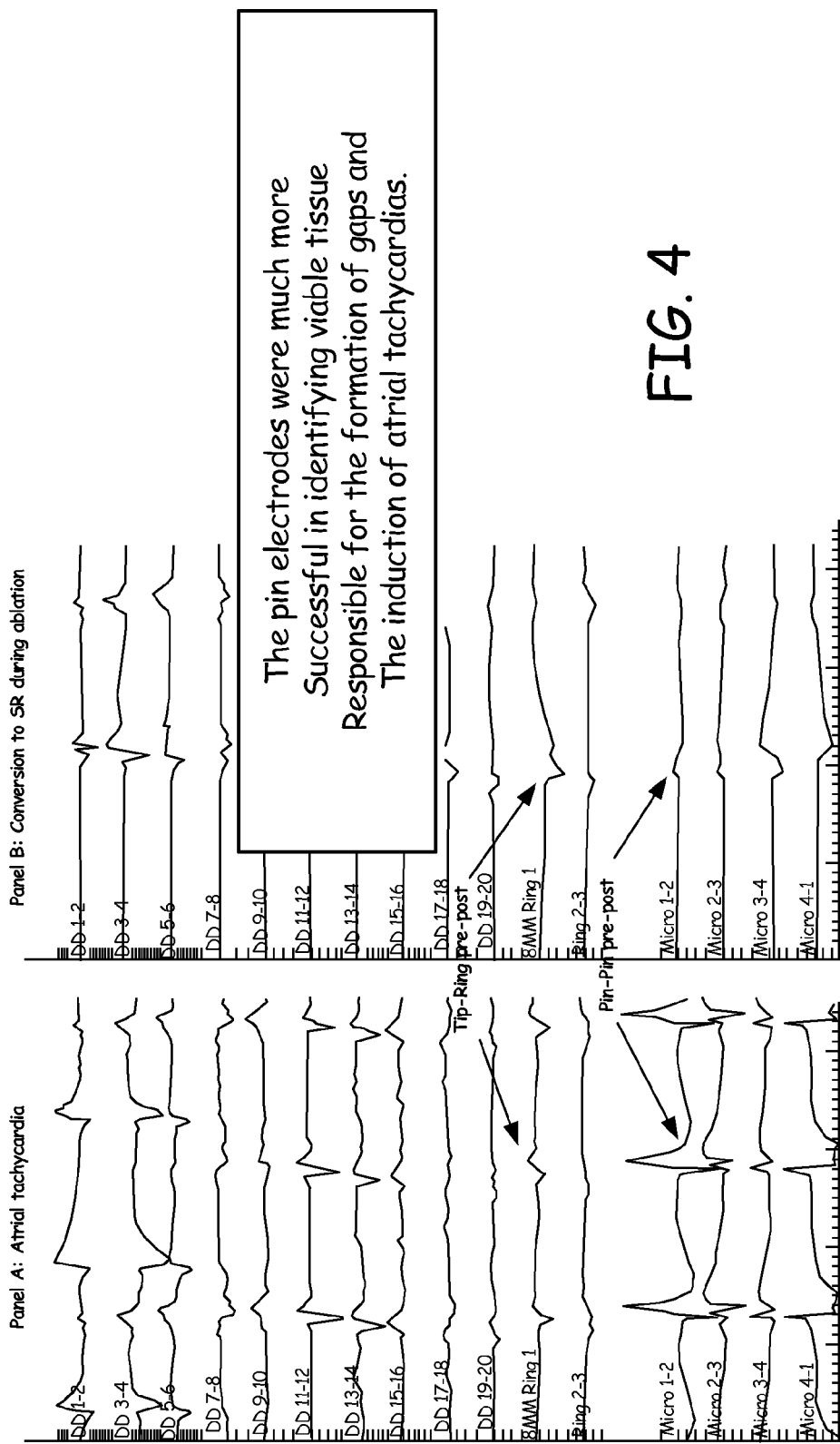
FIG. 4 illustrates a comparison of measured signal amplitude pre- and post-ablation during atrial tachycardia.

Exemplary catheters that can be used as the ablation catheter 2 can include those described in U.S. Patent App. Pub. Nos. US2008l0243214 entitled "High Resolution Electrophysiology Catheter," and 2010/0331658, entitled "Map and Ablate Open Irrigated Hybrid Catheter," which are hereby incorporated by reference in their entireties for all purposes. In various exemplary embodiments, the tissue ablation electrode 8 can have a length of between 6 and 14 mm, and a plurality of microelectrodes 9 equally spaced about the circumference of the tissue ablation electrode. In one embodiment, the tissue ablation electrode 8 can have an axial length of about 8 mm. In one embodiment, the ablation catheter 2 includes at least three microelectrodes 9 equally spaced about the circumference of the tissue ablation electrode 8 and at the same longitudinal position along the longitudinal axis of the tissue ablation electrode 8, the microelectrodes 9 forming at least first, second and third bipolar microelectrode pairs. In one embodiment, the catheter 2 includes a forward-facing microelectrode 9 generally centrally-located within the tissue ablation electrode 8. An exemplary such RF ablation catheter is illustrated in FIGS. 3 and 4 of the aforementioned U.S. Patent Application Pub. No. 2008/0243214.

In some embodiments, microelectrodes 9 can be located at other positions along the ablation catheter 2 in addition to or in lieu of the microelectrodes 9 in the tissue ablation electrode 8.

In various embodiments, the tissue ablation electrode 8 has an exterior wall that defines an open interior region (not shown). The exterior wall includes mapping electrode openings for accommodating the microelectrodes 9, and, in some embodiments, irrigation ports (not shown). The irrigation ports, when present, are in fluid communication an external irrigation fluid reservoir and pump (not shown) for supplying irrigation fluid to the myocardial tissue being mapped and/or ablated. Exemplary irrigated catheters for use as the catheter 2 can be any of the catheters described in the aforementioned U.S. Patent App. Pub. No. 2010/0331658. In various embodiments, the catheter system may also include noise artifact isolators (not shown), wherein the microelectrodes 9 are electrically insulated from the exterior wall by the noise artifact isolators.

In various embodiments, the mapping processor 4 is configured to detect, process, and record electrical signals within the heart via the ablation catheter 2. Based on these electrical signals, a physician can identify the specific target tissue sites within the heart, and ensure that the arrhythmia causing substrates have been electrically isolated by the ablative treatment. The mapping processor 4 is configured to process the output signals from the microelectrodes 9 and/or the ring electrodes 7, and to generate an output to a display (not shown) for use by the physician. In some embodiments, the display can include electrocardiograms (ECG) information, which can be analyzed by the user to determine the existence and/or location of arrhythmia substrates within the heart and/or determine the location of the ablation catheter 2 within the heart. In various embodiments, the output from the mapping processor 4 can be used to provide, via the display, an indication to the clinician about a characteristic of the ablation catheter 2 and/or the myocardial tissue being mapped.

The RF generator 3 is configured to deliver ablation energy to the ablation catheter 2 in a controlled manner in order to ablate the target tissue sites identified by the mapping processor 4. Ablation of tissue within the heart is well known in the art, and thus for purposes of brevity, the RF generator 3 will not be described in further detail. Further details regarding RF generators are provided in U.S. Pat. No. 5,383,874, which is expressly incorporated herein by reference. Although the mapping processor 4 and RF generator 3 are shown as discrete components, they can alternatively be incorporated into a single integrated device.

The RF ablation catheter 2 as described may be used to perform various diagnostic functions to assist the physician in an ablation treatment. For example, in some embodiments, the catheter is used to ablate cardiac arrhythmias, and at the same time provide real-time assessment of a lesion formed during RF ablation. Real-time assessment of the lesion may involve any of monitoring surface and/or tissue temperature at or around the lesion, reduction in the electrocardiogram signal, a drop in impedance, direct and/or surface visualization of the lesion site, and imaging of the tissue site (e.g., using computed tomography, magnetic resonance imaging, ultrasound, etc.). In addition, the presence of the microelectrodes within the RF tip electrode can operate to assist the physician in locating and positioning the tip electrode at the desired treatment site, and to determine the position and orientation of the tip electrode relative to the tissue to be ablated.

Figure 2:
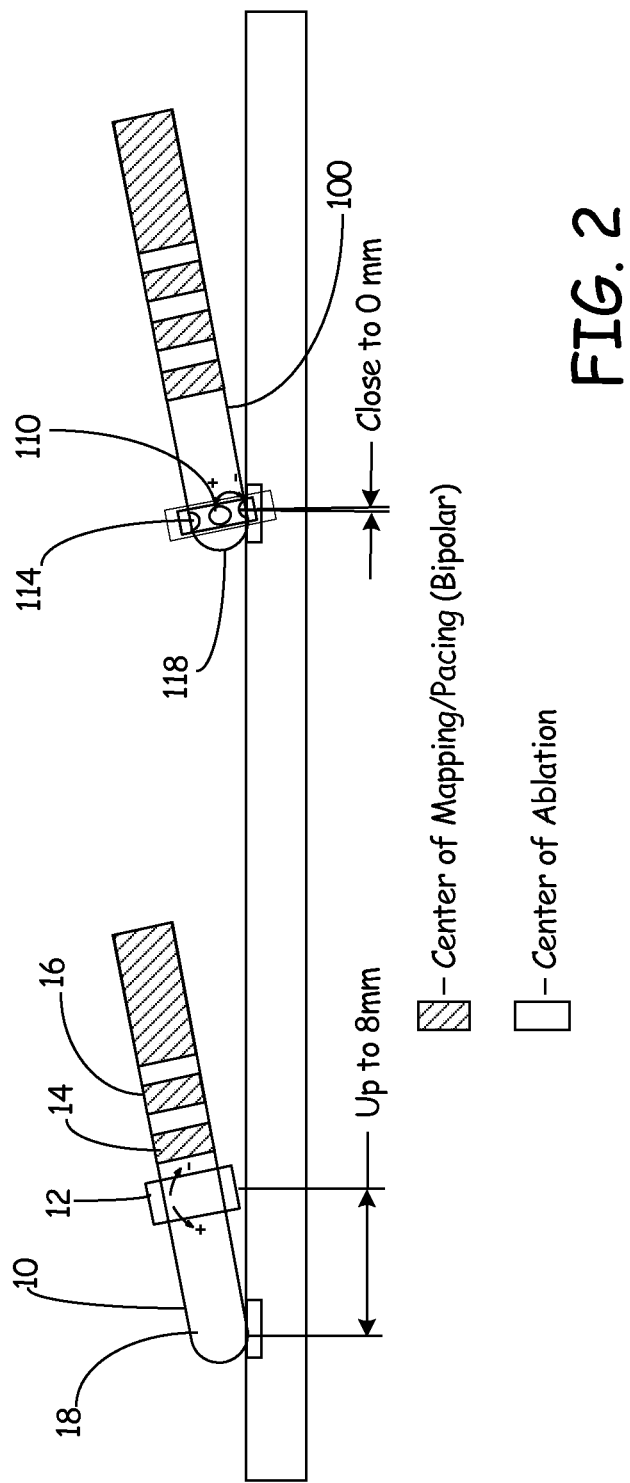
FIG. 2 is a schematic illustration showing a conventional ablation catheter on the left and an embodiment of a high-resolution ablation catheter of the present disclosure on the right.

FIG. 2 is a schematic illustration showing a conventional ablation catheter 10 (i.e., an ablation catheter lacking any microelectrodes within the tissue ablation electrode) on the left and an embodiment of a high-resolution ablation catheter 100 of the present disclosure on the right. For cardiac mapping, the conventional catheter relies on conventional ring electrodes 12, 14, 16 disposed along the mapping electrodes a distance from the ablation tip electrode 18, resulting in a large distance between the center of mapping/pacing and the center of ablation. The catheter of the present disclosure, in contrast, includes the mapping microelectrodes 110 in mapping electrode openings 114 in the ablation tip electrode 118 to allow the center of mapping/pacing to be in substantially the same location as the center of ablation.

FIG. 3 illustrates a comparison between changes in voltage (panel A) and frequency spectra (panel B) pre- and post-ablation for each of the catheters illustrated in FIG. 2. As is shown, the tip-to-ring signal changes in the conventional ablation catheter were minimal for both the voltage and frequency domains (arrows A and B). In contrast, the recorded changes from pin to pin (i.e., between mapping micro electrodes) in the catheter of the present disclosure were profound (arrows C and D).

FIG. 4 illustrates a comparison of measured signal amplitude pre- and post-ablation during atrial tachycardia. As shown, the tip-to-ring again signal changes in the conventional ablation catheter (top arrows) were small compared to the pin-to-pin signal changes. Thus, the pin electrodes were much more successful in identifying viable tissue responsible for the formation of gaps and the induction of atrial tachycardias.

Figure 5:
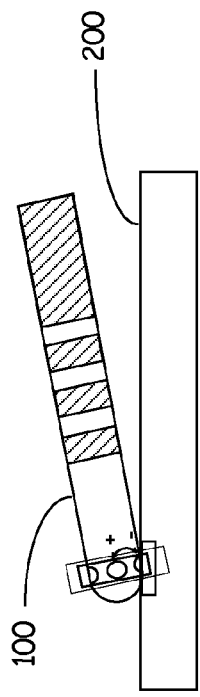
FIG. 5 is a schematic illustration showing the catheter of FIG. 2 oriented generally parallel to the surface of the cardiac tissue to be mapped and ablated.
Figure 6A:
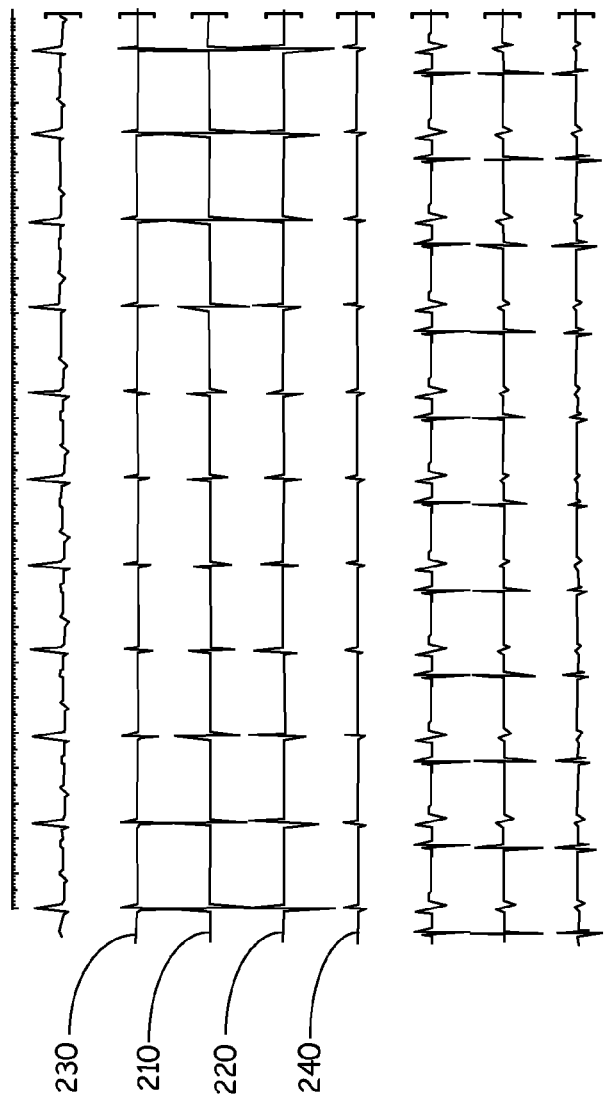
FIGS. 6A and 6B illustrate the amplitudes of the cardiac electrical signals sensed by the microelectrodes and also the ring electrodes on the catheter of FIG. 2.
Figure 6B:
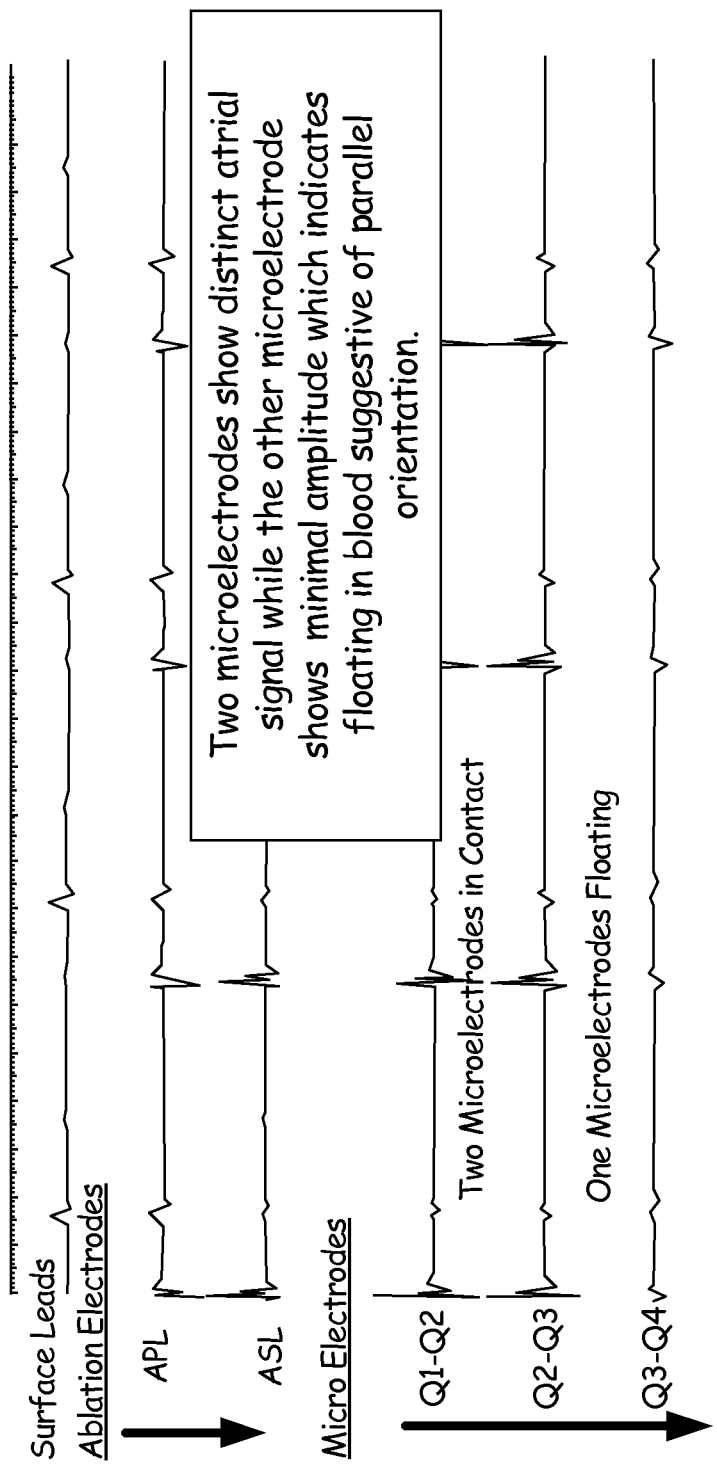

As explained previously, the microelectrodes 110 can advantageously provide feedback on electrode contact and tip electrode orientation within the heart. FIG. 5 is a schematic illustration showing the catheter 100 oriented generally parallel to the surface 200 of the cardiac tissue to be mapped and ablated. FIGS. 6A and 6B illustrate the amplitudes of the cardiac electrical signals sensed by the microelectrodes 110 and also the ring electrodes on the catheter 100, which data can be used to implement a method for determining electrode contact and the orientation of the catheter tip. In FIGS. 6A and 6B, the ECG traces of bipolar pairs of microelectrodes 110 are illustrated, as indicated by the labels defined and their corresponding ECG signals are illustrated. Specifically, in FIG. 6A, an ablation catheter having four microelectrodes (labeled 49, 50, 51 and 52) distributed about the circumference of the tissue ablation electrode, such that the labels 49-50, 50-51, 51-52 and 49-52 designate respective bipolar microelectrode pairs of adjacent microelectrodes. Similarly, in the example shown in FIG. 6B, the ECG traces for three bipolar microelectrode pairs (labeled Q1-Q2, Q2-Q3, and Q3-Q4) are illustrated.

In the illustrated example, as shown in FIG. 6A, two bipolar microelectrode pairs (indicated by references 210, 220) each show a distinct atrial signal while the other bipolar microelectrode pairs (indicated by references 230, 240) show minimal amplitude. The mapping microelectrode(s) with a signal of minimal amplitude indicates floating in blood, which is suggestive of a parallel tip orientation. FIG. 6B illustrates a similar result, with two of the bipolar microelectrode microelectrode pairs (the pairs Q1-Q2 and Q2-Q3) showing an atrial signal and one pair (Q3-Q4) showing a minimal signal amplitude. This data allows the system 1 to confirm both tip contact with the cardiac tissue as well as orientation of the tip relative to the tissue surface, which could not be accomplished using only the ring electrodes on the catheter 100, all of which show minimal signal amplitude (as shown in FIGS. 6A and 6B) suggesting no tissue contact.

Figure 7:
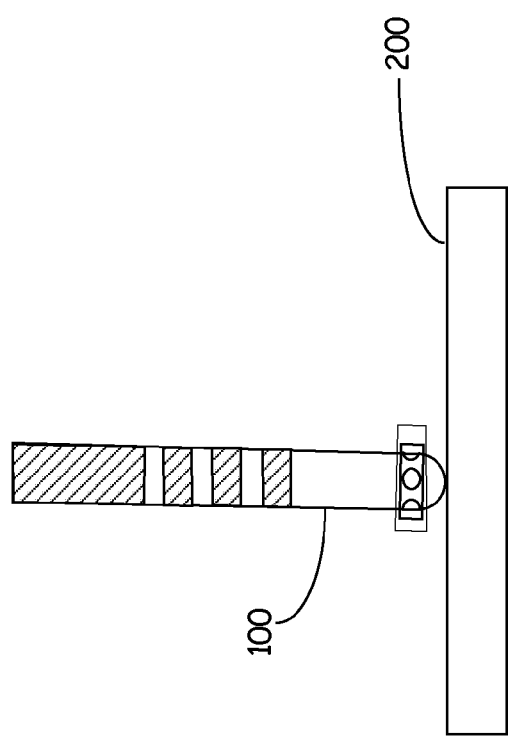
FIG. 7 is a schematic illustration showing the catheter of FIG. 2 oriented generally perpendicular to the surface of the cardiac tissue to be mapped and ablated.
Figure 8:
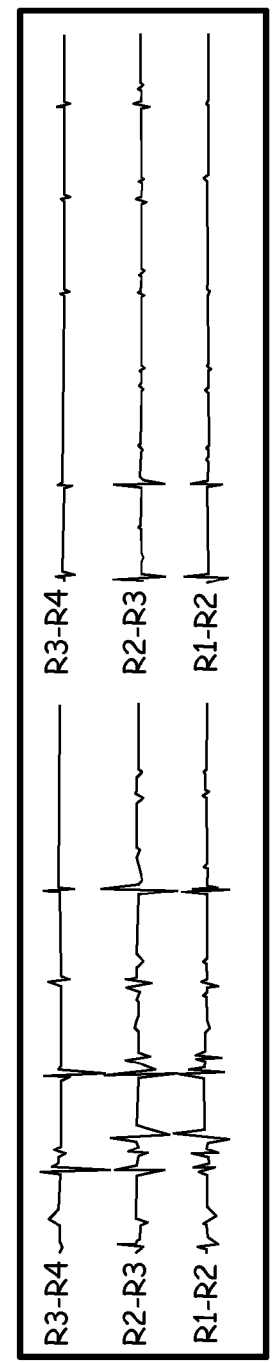
FIG. 8 illustrates the corresponding electrogram signals for the configuration of FIG. 7.

FIG. 7 is a schematic illustration showing the catheter 100 oriented generally perpendicular to the surface 200 of the cardiac tissue to be mapped and ablated, and FIG. 8 illustrates the corresponding electrogram signals for the configuration of FIG. 7. As can be seen in FIG. 8, all bipolar microelectrode pairs (designated by R3-R1, R2-R3 and R1-R2) show substantially equal signal amplitude, indicating that all of the microelectrodes are floating in blood and not in contact with the surface 200.

Figure 9:
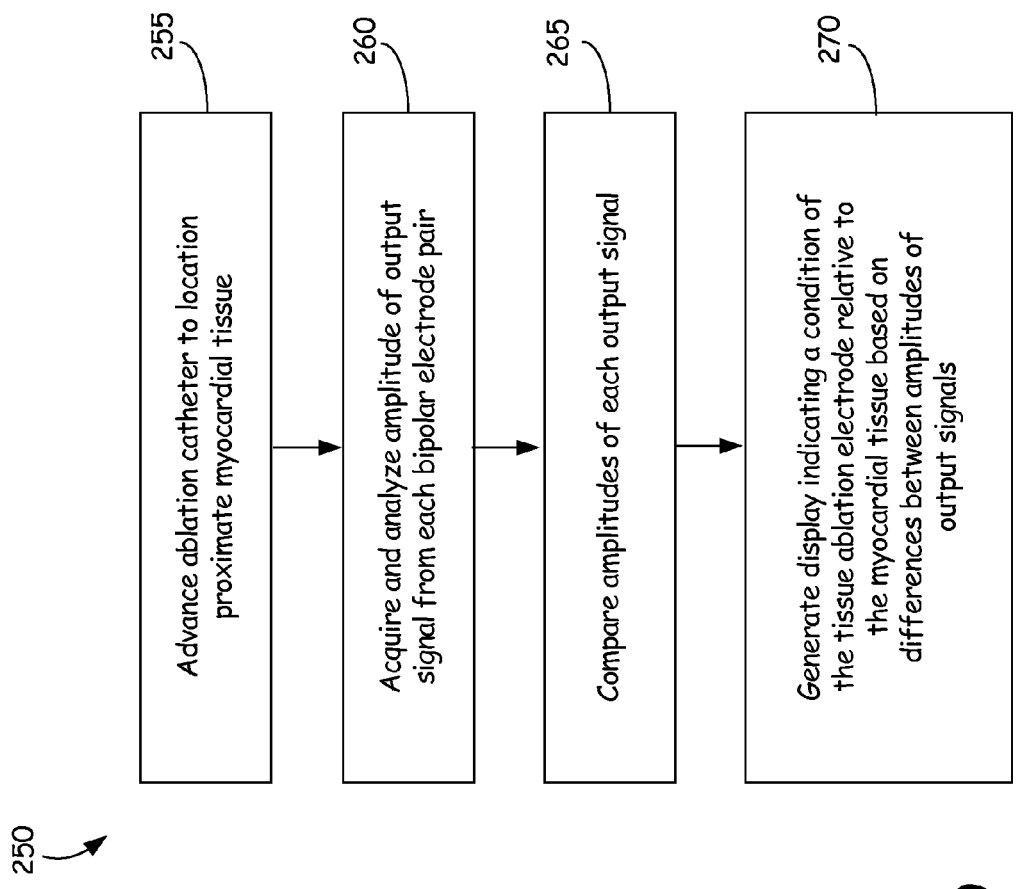
FIG. 9 is a flow chart illustrating a method for assessing a characteristic (e.g., tissue contact) of the tissue ablation electrode of the ablation catheter of FIG. 1 or 2 according to the various embodiments.

FIG. 9 is a flow chart illustrating a method 250 for assessing a characteristic (e.g., tissue contact) of the tissue ablation electrode of the ablation catheter 2, 100 according to the various embodiments as described herein. As shown in FIG. 9, the method 250 includes, at step 255, first advancing the distal portion of the ablation catheter intravascularly to a location proximate the myocardial tissue to be mapped and/or ablated. The ablation catheter may be the ablation catheter 2 or 100 described herein. In the various embodiments, the particular ablation catheter includes a plurality of microelectrodes in the tissue ablation electrode defining a plurality of bipolar pairs of microelectrodes. In one embodiment, the ablation catheter includes at least three microelectrodes disposed about the circumference of the tissue ablation electrode defining first, second and third bipolar microelectrode pairs.

Next, at step 260, the system acquires the output signal from each bipolar electrode pair. Subsequently, as shown at step 265, the method compares the amplitude of the output signal from each of the bipolar microelectrode pairs to the amplitudes of the output signals from the other of the plurality of bipolar microelectrode pairs. Then, as indicated at step 70, a display is generated indicating a condition of the tissue ablation electrode relative to the myocardial tissue based on differences between amplitudes of output signals.

In one embodiment, the displayed condition can include a visual indication of the proximity of the tissue ablation electrode to the myocardial tissue. In one embodiment, this visual indication of proximity can include an indication that the tissue ablation electrode is in contact with the myocardial tissue if the difference between the amplitude of any one of the output signals and the amplitude of any one or more of the other output signals exceeds a predetermined threshold. In addition, the visual indication of proximity can include an indication that the tissue ablation electrode is not in contact with the myocardial tissue if the difference between the amplitude of any one of the output signals and the amplitude of any one or more of the other output signals does not exceed a predetermined threshold.

In various embodiments, the steps of acquiring and comparing the output signals from the bipolar microelectrode pairs are performed by the mapping processor, which is operatively coupled to the microelectrodes (see FIG. 1).

In one embodiment, the microelectrodes, and consequently, the first, second and third bipolar microelectrode pairs, each have a known position with respect to the tissue ablation electrode and the other microelectrodes. In such embodiments, the method 250 can further include displaying to the clinician a visual indication of the orientation of the tissue ablation electrode relative to the myocardial tissue based on the amplitudes of the output signals from the first, second and third bipolar microelectrode pairs.

In one embodiment, the method 250 can be carried out using an irrigated ablation catheter having a plurality of irrigation ports in the tissue ablation electrode fluidly and operatively coupled to an irrigation fluid reservoir and pump, and the method 250 includes supplying an irrigation fluid through the irrigation ports during the mapping and/or ablation procedures.

Figure 10:
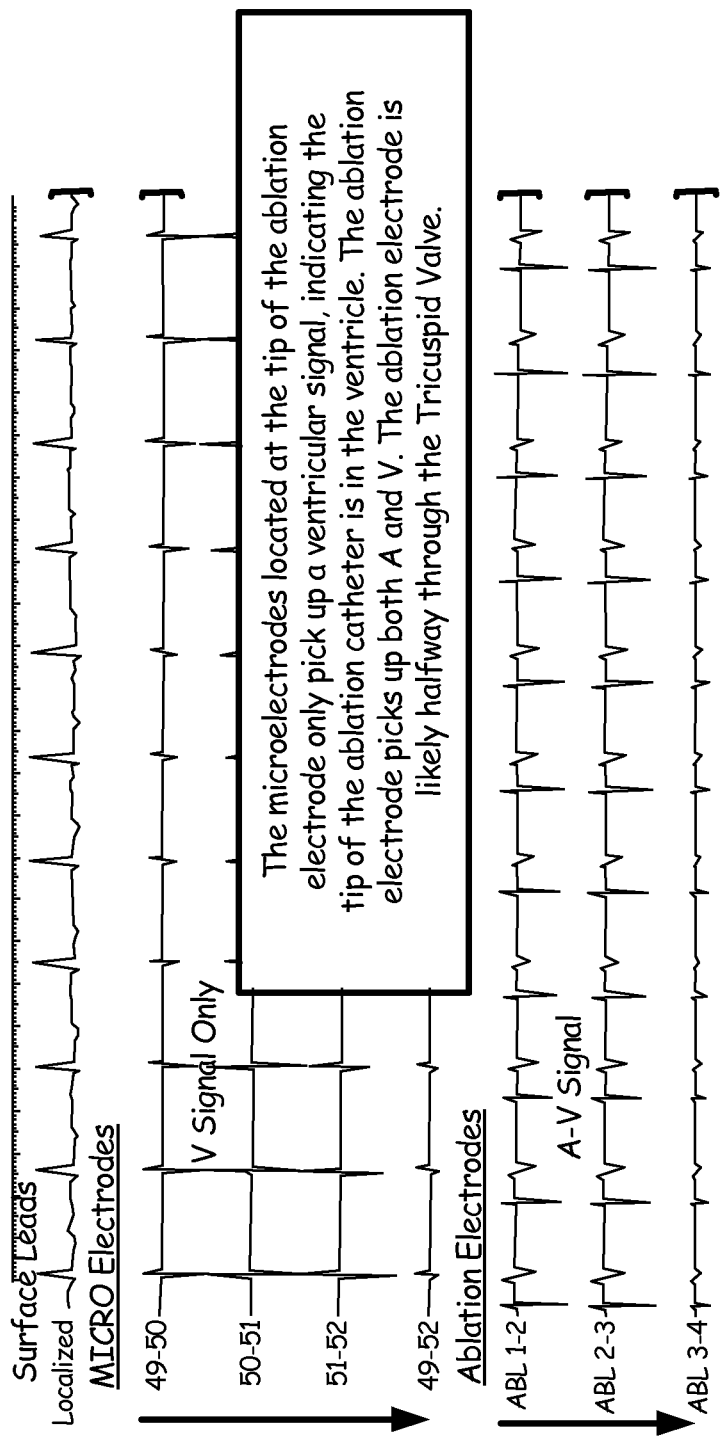
FIG. 10 illustrates an output from a plurality of bipolar microelectrode pairs that can be used by the system of FIG. 1 in a method for determining the tip location when far field noise is suspected.

Still other methods may advantageously be facilitated by the presence and configurations of the microelectrodes of the ablation catheters 2, 100 described herein. For example, FIG. 10 illustrates an ECG generated from an output from a plurality of bipolar microelectrode pairs (labeled 49-50, 50-51, 51-52 and 49-52, respectively) that can be used by the system 1 in a method for determining the tip location when far field noise is suspected. In the example shown, the microelectrodes located at the tissue ablation electrode only pick up a ventricular signal, indicating the tissue ablation catheter is in the ventricle. On the other hand, the ring electrodes pick up both atrial and ventricular signals. Based on these signals, it may be determined that the ablation electrode is likely halfway through the tricuspid valve.

Figure 11:
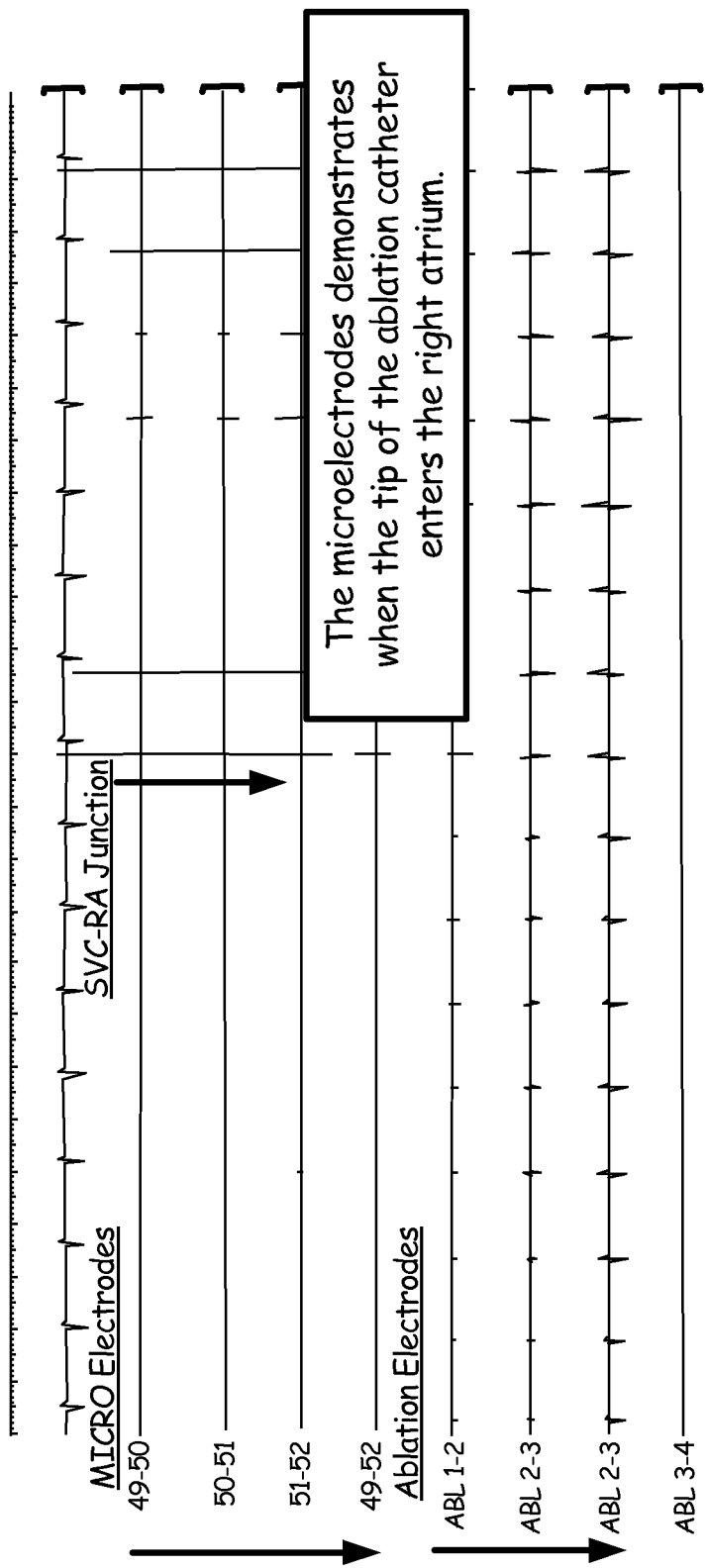
FIG. 11 illustrates an output from a plurality of bipolar microelectrode pairs that can be used by the system of FIG. 1 in a method for discerning different tissue types as the catheter navigates between different cardiac structures.

FIG. 11 illustrates an ECG generated from an output from a plurality of bipolar microelectrode pairs (labeled 49-50, 50-51, 51-52 and 49-52, respectively) that can be used by the system 1 in a method for discerning different tissue types as the catheter navigates between different cardiac structures. In the embodiment shown, the microelectrodes exhibit minimal response as the catheter is located within the superior vena cava. When the catheter exits the superior vena cava and enters the right atrium, the signals generated by the microelectrodes change substantially.

Figure 12:
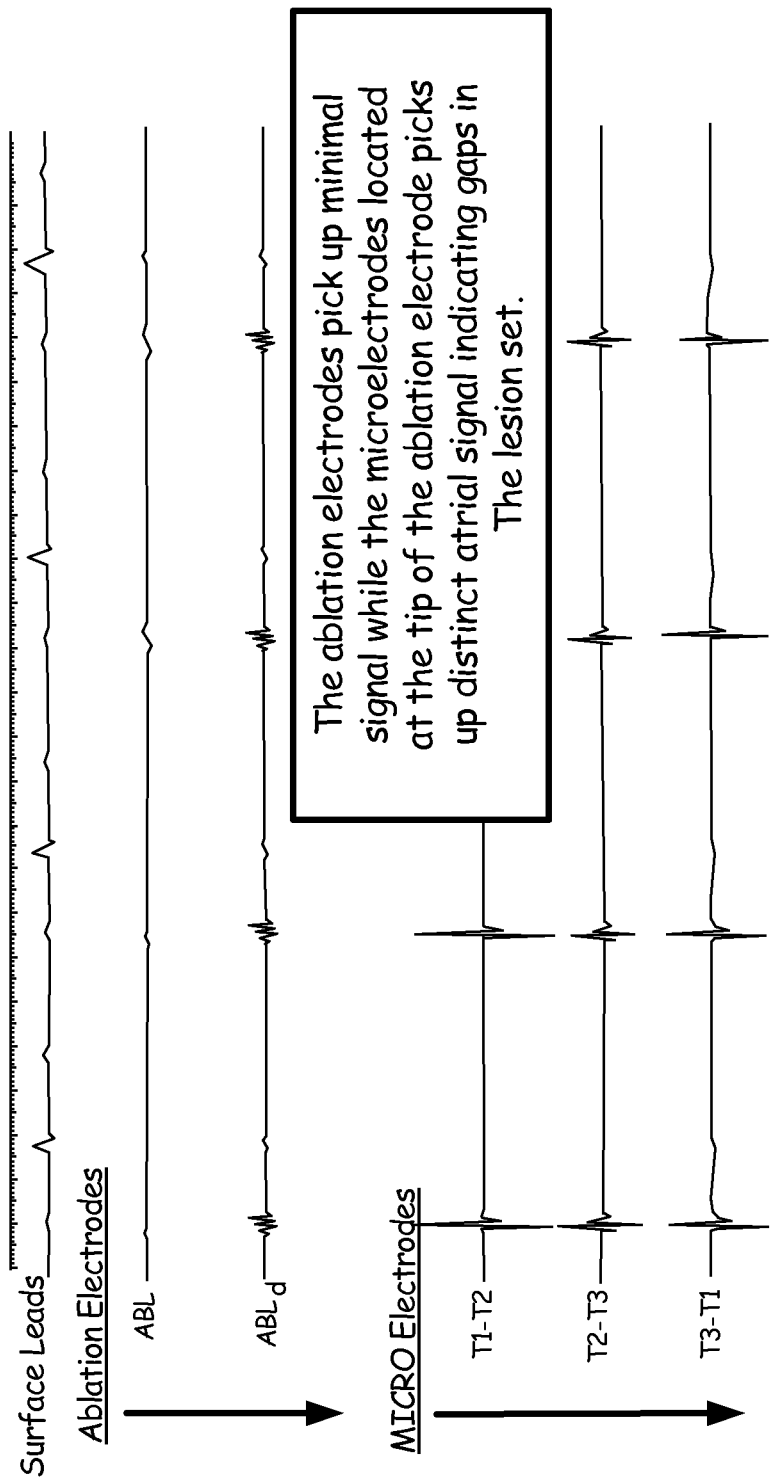
FIG. 12 illustrates an output from a plurality of bipolar microelectrode pairs that can be used by the system of FIG. 1 in a method for identifying gaps in lesion sets based on a comparison of signals between the ablation electrodes and microelectrodes.

FIG. 12 illustrates an ECG generated from an output from a plurality of bipolar microelectrode pairs (labeled T1-T2, T2-T3, T3-T1, respectively) that can be used by the system 1 in a method for identifying gaps in lesion sets. In the example illustrated, the ablation electrodes pick up minimal signals while the microelectrodes located at the tip of the ablation electrode picks up distinct atrial signals, indicating gaps in the lesion set. Thus, in an exemplary method, the mapping processor 4 can identify distinct intrinsic cardiac activation signals in the output signals from the bipolar microelectrode pairs, and thereafter generate an output to a display to identify the corresponding gaps in the lesion sets based on the locations of those bipolar microelectrode pairs. In various embodiments, the mapping processor 4 can further acquire output signals from the ring electrodes 7 (or bipolar pairs defined by two ring electrodes 7 or a ring electrode 7 and the tissue ablation electrode 8) (see FIG. 1), compare the output signals from the bipolar microelectrode pairs to corresponding outputs from the ring electrodes, and use this comparison in identifying the intrinsic activation signals and corresponding gaps in lesion sets.

Figure 13:
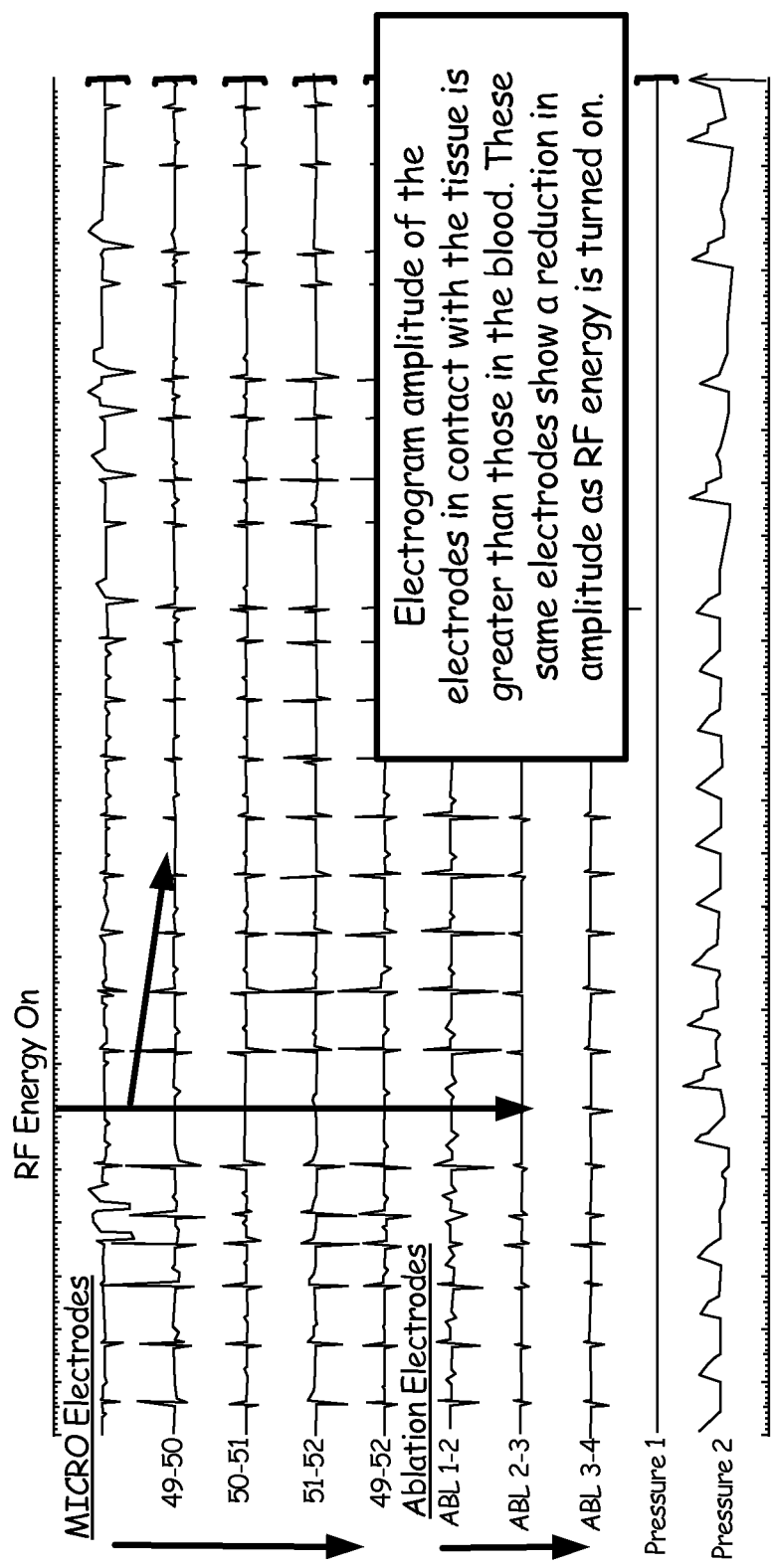
FIG. 13 illustrates an output from a plurality of bipolar microelectrode pairs that can be used by the system of FIG. 1 in a method for assessing electrogram attenuation during ablation.

FIG. 13 illustrates an ECG generated from an output from a plurality of bipolar microelectrode pairs (labeled 49-50, 50-51, 51-52 and 49-52, respectively) that can be used by the system 1 in a method for assessing electrogram attenuation during ablation. In the illustrated example, the electrogram amplitude of the microelectrodes in contact with the tissue is greater than those in the blood. When the RF energy is turned on during ablation, the microelectrodes show a reduction in amplitude.

Figure 14:
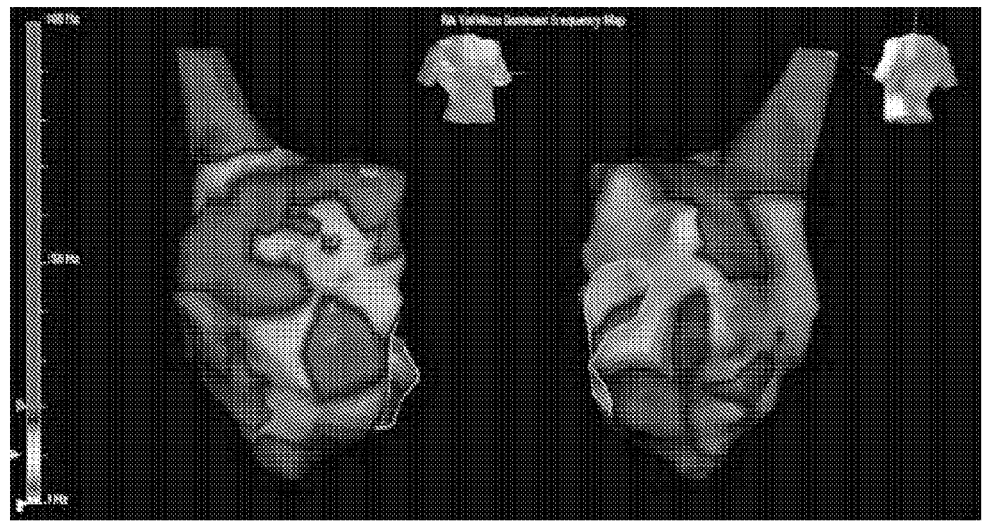
FIGS. 14 and 15 illustrate exemplary electroanatomical maps generated using a catheter including high-resolution microelectrodes according to embodiments of the invention.
Figure 14:
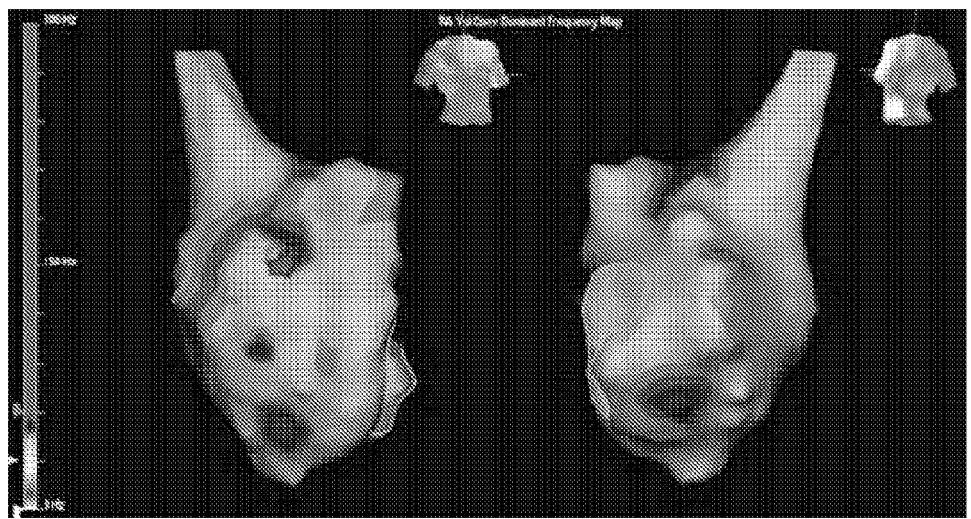
Figure 15:
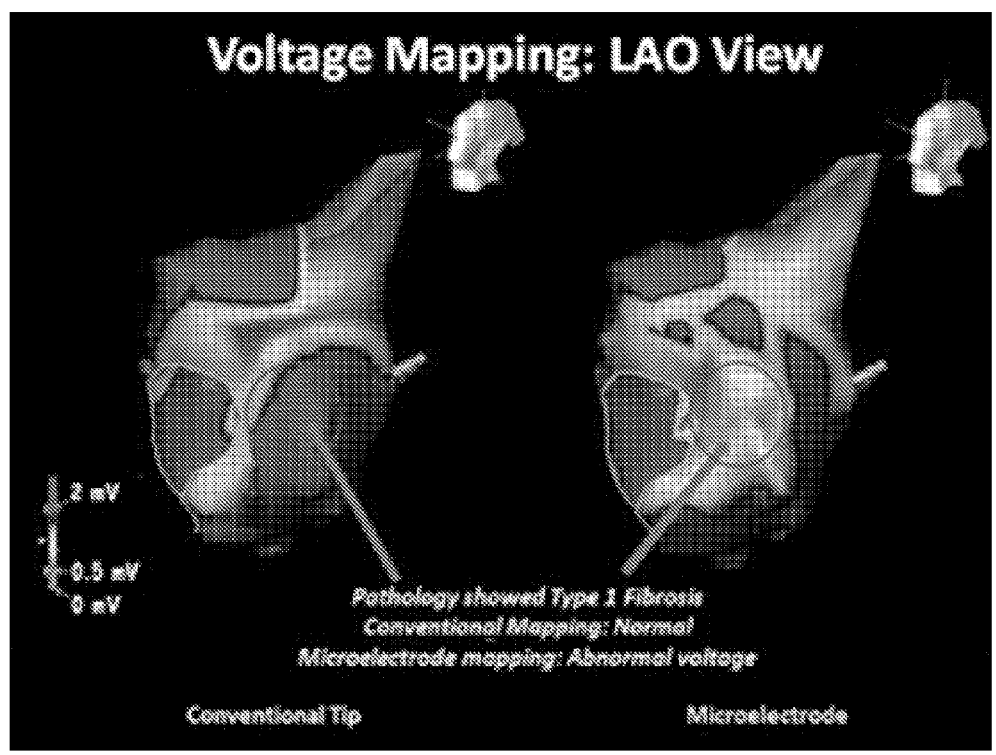

The microelectrode ablation catheters 2, 100 of the various embodiments can also advantageously be integrated with a three-dimensional cardiac mapping system for generating high-resolution electroanatomical maps of the heart for aiding the physician in diagnosing cardiac arrhythmias (e.g., atrial fibrillation), identifying a treatment regime (e.g., ablation procedures such as pulmonary vein isolation) and verifying the sufficiency of the treatment. FIGS. 14 and 15 illustrate exemplary electroanatomical maps 300, 400, 500, 600. In FIG. 14, the map 300 is an exemplary dominant frequency map generated using a conventional ablation catheter such as the catheter 10 in FIG. 2, and the map 400 is an exemplary dominant frequency map generated using the catheter 2 of FIG. 1 or the catheter 100 of FIG. 2 including the plurality of microelectrodes spatially located within the RF ablation electrode. The particularly high signal fidelity provided by the mini-electrodes of the catheter 2, 100 allows the physician to accurately identify abnormal tissue substrates found in fibrotic tissue, thus allowing the physician to more readily discern different tissue types and identify substrates to be ablated (e.g., by analysis of homogeneous or heterogeneous depolarization) than can be accomplished using the conventional ablation catheter 10 of FIG. 2. The advantages provided by the catheter 2, 100 is illustrated in FIG. 15, showing a comparison of electroanatomical maps generated by an exemplary conventional catheter 10 and the catheter 100 of the various embodiments on cardiac tissue confirmed by pathology to exhibit Type 1 fibrosis. As can be seen in FIG. 15 (left image), the map generated using the conventional catheter 10 showed normal voltage distribution within the fibrotic tissue. In contrast, the map generated using the catheter 2, 100 (right image) with the microelectrodes 9, 110 (FIGS. 1, 2 respectively) confirms abnormal voltages in the fibrotic tissue.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:
1. An electrophysiology system comprising:
   an ablation catheter including:
      a flexible catheter body having a distal portion;
      a tissue ablation electrode configured to apply ablation energy to the myocardial tissue;
      a plurality of microelectrodes circumferentially distributed about the tissue ablation electrode and electrically isolated therefrom, the plurality of microelectrodes defining a plurality of bipolar microelectrode pairs, each bipolar microelectrode pair configured to generate an output signal based on a cardiac activation signal;
   a radiofrequency (RF) generator operatively coupled to the tissue ablation electrode for generating the ablation energy to be conveyed to the tissue ablation electrode; and
   a mapping processor configured to:
      acquire the output signals from each of the bipolar microelectrode pairs;
      compare an amplitude of the output signal from each of the bipolar microelectrode pairs to the amplitudes of the output signals from the other of the plurality of bipolar microelectrode pairs; and
      generate an output to a display to provide a clinician with a visual indication of a proximity of the tissue ablation electrode to the myocardial tissue, the visual indication including:
         an indication that the tissue ablation electrode is in contact with the myocardial tissue if, based on the comparison between the amplitudes of the output signals, a difference between the amplitude of any one of the output signals and the amplitude of any one or more of the other output signals exceeds a predetermined threshold; and
         an indication that the tissue ablation electrode is not in contact with the myocardial tissue if, based on the comparison between the amplitudes of the output signals, the difference between the amplitude of any one of the output signals and the amplitude of any one or more of the other output signals does not exceed a predetermined threshold.

2. The system of claim 1, wherein the plurality of microelectrodes include three microelectrodes defining first, second and third bipolar microelectrode pairs.

3. The system of claim 2, wherein the three microelectrodes are disposed at the same longitudinal position along the tissue ablation electrode.

4. The system of claim 3, wherein the mapping processor is further configured to generate an output to a display to provide the clinician with a visual indication of an orientation of the tissue ablation electrode relative to the myocardial tissue based on the amplitudes of the output signals from the first, second and third bipolar microelectrode pairs.

5. The system of claim 1, wherein the mapping processor is further configured to acquire output signals from one or more ring electrodes located on the ablation catheter proximal to the tissue ablation electrode, compare the output signals from the bipolar microelectrode pairs with the ring electrode output signals to identify sensed intrinsic cardiac activation signals in the bipolar microelectrode pair output signals, and generate an output to the display indicating a gap in an ablation lesion pattern at the location of the bipolar microelectrode pairs that sensed the intrinsic cardiac activation signals.

6. The system of claim 1, wherein the ablation catheter further comprises a plurality of irrigation ports in the tissue ablation electrode fluidly and operatively coupled to an irrigation fluid reservoir and pump.

7. The system of claim 1, wherein the ablation catheter further includes a proximal handle having a control element for manipulation by a user, and wherein the distal portion of the ablation catheter is deflectable upon manipulation of the control element.

* * * * *